(12) United States Patent
Vleugels

(10) Patent No.: US 12,064,204 B2
(45) Date of Patent: Aug. 20, 2024

(54) SURGICAL INSTRUMENT

(71) Applicant: EFI Holding B.V., Maastricht (NL)

(72) Inventor: Michel Petronella Hubertus Vleugels, Maastricht (NL)

(73) Assignee: EFI Holding B.V., Maastricht (NL)

( * ) Notice: Subject to any disclaimer, the term of this patent is extended or adjusted under 35 U.S.C. 154(b) by 871 days.

(21) Appl. No.: 16/254,917

(22) Filed: Jan. 23, 2019

(65) Prior Publication Data
US 2020/0155258 A1     May 21, 2020

(30) Foreign Application Priority Data
Nov. 16, 2018 (NL) ..................................... 2022018

(51) Int. Cl.
| | |
|---|---|
| A61B 34/00 | (2016.01) |
| A61B 17/29 | (2006.01) |
| A61B 17/00 | (2006.01) |
| A61B 90/00 | (2016.01) |

(52) U.S. Cl.
CPC .............. A61B 34/76 (2016.02); A61B 17/29 (2013.01); *A61B 2017/00075* (2013.01); *A61B 2017/00734* (2013.01); *A61B 2017/2903* (2013.01); *A61B 2017/2925* (2013.01); *A61B 2090/064* (2016.02)

(58) Field of Classification Search
CPC ..................... A61B 34/76; A61B 17/29; A61B 2017/00075; A61B 2017/00734; A61B 2017/2903; A61B 2017/2925; A61B 2090/064
See application file for complete search history.

(56) References Cited

U.S. PATENT DOCUMENTS

| | | | |
|---|---|---|---|
| 5,609,607 A | 3/1997 | Hechtenberg et al. | |
| 5,762,256 A | 6/1998 | Mastri et al. | |
| 6,491,649 B1 | 12/2002 | Ombrellaro | |
| 2010/0152586 A1 | 6/2010 | Grant et al. | |
| 2010/0179587 A1 | 7/2010 | Grant et al. | |
| 2012/0010506 A1* | 1/2012 | Ullrich ..................... | A61B 8/12 |
| | | | 600/440 |
| 2012/0143182 A1 | 6/2012 | Ullrich et al. | |

FOREIGN PATENT DOCUMENTS

| | | |
|---|---|---|
| EP | 2 277 458 A1 | 1/2011 |
| JP | H8-90458 A | 4/1996 |

OTHER PUBLICATIONS

Search Report and Written Opinion, Application No. NL 2022018, dated Jul. 17, 2019.

* cited by examiner

*Primary Examiner* — Anh T Dang
(74) *Attorney, Agent, or Firm* — Hoffmann & Baron, LLP

(57) ABSTRACT

The invention provides surgical instrument, for example surgical instrument for minimally invasive surgery, comprising:
  an elongate frame,
  at least one jaw element mounted movably at a distal end of the elongate frame,
  a trigger device to operate the at least one jaw element and arranged at a proximal end of the elongate frame,
  an actuation rod provided between the trigger device and the at least one jaw element to transfer movement of the trigger device to the at least one jaw element,
  a sensor to provide a sensor signal representative for a force exerted on the at least one jaw element, and
  a tactile feedback device to provide tactile feedback to the user on the basis of the sensor signal, wherein the tactile feedback device is mounted on the elongate frame.

27 Claims, 4 Drawing Sheets

SURGICAL INSTRUMENT

THE FIELD OF THE INVENTION

The present invention relates to a surgical instrument, for example a surgical instrument for minimally invasive surgery. The invention also relates to the use of the surgical instrument 1 to detect heartbeat related pulsation of tissue and a method to detect pulsation of tissue.

BACKGROUND OF THE INVENTION

U.S. Pat. No. 5,609,607 discloses a surgical instrument comprising an elongate frame. At the distal of the elongate frame two forceps jaw elements are provided. The forceps jaw elements are operated by grips arranged at the proximal end of the frame. On the inner surface of each of the jaw elements a sensor array is arranged. The sensor arrays are sensitive to force and pressure. The sensor arrays supply analog electric sensor signals to a display when objects are touched and gripped.

With the aid of the sensor signals, the tissue structure is modeled/simulated in an actuator array, located in the grips of the forceps. The surface of these actuator array is felt with the fingertip(s) holding the grips. In this manner, the grip and feel of organs inside the body are conveyed to the outside.

A drawback of the known surgical instrument is that the sensor arrays may give insufficient tactile feedback for the user. For example, the pulsation of tissue, such as heartbeat related pulsation of tissue cannot properly be detected by the known embodiment of a surgical instrument.

SUMMARY OF THE INVENTION

An object of the present invention is to provide a surgical instrument with improved tactile feedback to the user, or at least to provide a surgical instrument with an alternative tactile feedback device.

The present invention provides a surgical instrument, for example surgical instrument for minimally invasive surgery, comprising:
an elongate frame,
at least one jaw element mounted movably at a distal end of the elongate frame,
a trigger device to operate the at least one jaw element and arranged at a proximal end of the elongate frame,
an actuation rod provided between the trigger device and the at least one jaw element to transfer movement of the trigger device to the at least one jaw element,
a sensor to provide a sensor signal representative for a force exerted on the at least one jaw element, and
a tactile feedback device to provide tactile feedback to the user on the basis of the sensor signal, wherein the tactile feedback device is mounted on the elongate frame.

It has been found that mounting the tactile feedback device on the elongate frame instead of mounting the tactile feedback device on the trigger device itself, provides improved results with respect to the feedback that is provided to the user. For example, the pulsation of tissue, in particular heartbeat related pulsation of tissue is better perceived by the user when the location of feedback, i.e. the location of the tactile feedback device, is decoupled from the location where a force is exerted by the user to operate the at least one jaw element, i.e. the location where the trigger device manipulated by the user. Heartbeat related pulsation of tissue is pulsation of tissue caused by the beating of the heart, for example the pulsation of an artery or of tissue adjacent to an artery.

In an embodiment, the tactile feedback device comprises:
a tactile element to provide tactile feedback to the user,
a tactile element guide supporting the tactile element, wherein the tactile element is movable, for example linearly movable, with respect to the tactile element guide in a range of movement between an outer position and an inner position, and
a feedback actuator arrange to move the tactile element within in the range of movement with respect to the tactile element guide. In the outer position, the tactile element protrudes partly from a housing of the surgical instrument, for example a housing of a handle part of the surgical instrument, and in inner position the tactile element is retracted in the housing of the surgical instrument.

The tactile element may be any element that can be moved with respect to the tactile element guide to provide tactile feedback to the user. The movement may be any movement such as a linear or rotating movement. The tactile element and the tactile element guide may be separate elements, or may be flexibly connected to each other.

The tactile element guide may be mounted on the elongate frame, for example an inner frame or a housing of the handle part.

The tactile element has a tactile end surface arranged to receive a body part thereon. By actuation of the tactile element in the range of movement, the tactile end surface may be pushed against the body part, for example a finger, of the user. The user will feel this pushing of the tactile element on the body part.

The tactile end surface is preferably arranged to receive a finger tip of the user. A fingertip, for example a fingertip of the index finger or middle finger has been found as a very suitable skin surface to provide tactile feedback to the user.

In an embodiment, the tactile element has a tactile end surface and the tactile element guide comprises a guide end surface, wherein in at least one position of the tactile element the guide end surface is substantially flush with the tactile end surface such that in at least this position of the tactile element a body part of the user placed on the tactile element will be in contact with both the guide end surface and the tactile end surface.

The guide end surface that in at least one position of the tactile element is substantially flush with the tactile end surface has the advantage that at least in this position a body part of the user placed on the tactile element will be in contact with both the guide end surface and the tactile end surface. When touching both the guide end surface of the tactile element guide and the tactile end surface of the tactile element, movement of the tactile element with respect to the tactile element guide can be better perceived by the user.

In an embodiment, the tactile end surface comprises one or more surface areas and the tactile guide surface at least one surface area, wherein the one or more surface areas of the tactile end surface are at least provided at two opposite sides of at least one surface area of the guide end surface, wherein the one or more surface areas of the tactile end surface and the at least one surface area of the guide end surface are designed to be simultaneously touched by a single finger tip of a user, when the tactile element is arranged in the at least one position in which the guide end surface is substantially flush with the tactile end surface.

The tactile feedback may be further improved by arranging one or more surface areas of the tactile end surface at opposite sides of at least one surface area of the guide end surface. It has been found that when a central area of a fingertip is arranged on the at least one surface area of the guide end surface, movement of the tactile element, transferred to the fingertip surface by the one or more surface areas of the tactile end surface arranged at at least two opposite sides of the at least one surface area of the guide end surface, can be properly felt by the user.

It is remarked that the one or more surface areas of the tactile end surface and the at least one surface area of the guide end surface, when positioned to form a substantially flush surface area, together may form a concave surface suitable to mate with an average sized convex surface of a fingertip of for example an index finger or middle finger of a user.

In an embodiment, the tactile end surface comprises a horse shoe shape or at least partly annular shape. In such embodiment the horse shoe shape or at least partly annular shape form the one or more surface areas of the tactile end surface that are arranged at at least two opposite sides of a central surface area formed by the guide end surface.

An outer diameter of the horse shoe shape or at least partly annular shape may for example be 5 mm to 18 mm, preferably 6 mm to 10 mm.

In an embodiment, the feedback actuator comprises a linear voice coil actuator. A linear voice coil motor is a suitable actuator to move the tactile element with respect to the tactile element guide in order to provide feedback to the user. A linear voice coil actuator is for example suitable to provide feedback on heartbeat related pulsation of tissue touched by the at least one jaw element.

In alternative embodiments, other types of actuators, preferably linear actuators may be used to move the tactile element on the basis of the sensor signal. Examples of linear motors that may be applied in a tactile feedback device are a linear DC motor, a solenoid, a piezo motor, a shape memory alloy actuator. Other types of suitable motors may for example be a DC rotation motor, a voice coil rotation motor, a linear pneumatic or linear hydraulic motor.

In an embodiment, the tactile element is biased by a biasing element in the outer position. When a body part, for example a finger is arranged on the tactile element, the tactile element may be pushed from the outer position to a position where an tactile end surface of the tactile element and an guide end surface of the tactile element guide are substantially flush, i.e. both the tactile end surface and the guide end surface are in contact with the respective finger of the user. This is a suitable start position for providing tactile feedback to the user. Furthermore, the biasing element, for example a spring, may improve that the tactile element remains pushed against the finger in the range of movement of the tactile element to the outer position.

In an embodiment, the tactile feedback device comprises an activation sensor, wherein the activation sensor is arranged to determine whether the tactile element is arranged in the outer position or not, and wherein the tactile feedback device is configured to be deactivated when the tactile element is arranged in the outer position and wherein the tactile feedback device is configured to be activated when the tactile element is not arranged in the outer position.

The tactile feedback device, when activated uses energy. In an embodiment of the surgical instrument, the energy is provided by a battery. To prevent that energy is used when the tactile feedback device is not used, the tactile feedback is only activated when the tactile element is moved out of the outer position. This movement out of the outer position may typically be applied when a body part, for example a finger is placed on the tactile element, as explained above.

The activation sensor may be any sensor that is capable of determining whether the tactile element is in the outer position or not. The activation sensor is for example an optical sensor having a light source to provide a light beam towards a light detector, wherein the light beam is only blocked or only non-blocked by a part of the tactile element of movable part of the feedback actuator when the tactile element is in the outer position.

In an embodiment, a bandwidth of the tactile feedback device is designed to provide tactile feedback of heartbeat related pulsation of tissue manipulated by the at least one jaw element. The tactile feedback device of the invention may be used to provide tactile feedback of heartbeat related pulsation of tissue manipulated by the at least one jaw element. This heartbeat related pulsation is very useful information for a surgeon. To ensure that the heartbeat related pulsation is felt by the user, the different components of the feedback loop, such as the sensor, a controller and the tactile feedback device, for example an actuator of the tactile feedback device is provided with sufficient bandwidth to provide feedback on the heart beat related pulsation of tissue. The bandwidth with which the feedback may be provided is for example in the range of 0.5 Hz to 4 Hz, such as in the range of 0.8 to 3.5 Hz.

In an embodiment, the trigger device comprises a trigger having a gripping element designed to receive a thumb of the user, wherein the gripping element is arranged at a proximal side of the surgical instrument. The tactile feedback device is arranged on the frame of the surgical instrument and not on the trigger device. further, it is desirable that a finger, for example a fingertip of the index finger or middle finger of a user is used to provide feedback to the user. This means that this body part/finger used for feedback with the tactile feedback device cannot be used for manipulation of the trigger device. By providing a trigger device at the proximal side of the surgical instrument that can be manipulated by a thumb of a user, the manipulation of the trigger device and the receipt of feedback can be performed by a single hand, which simultaneously also carries the surgical instrument.

In an embodiment, the tactile feedback device is arranged to provide a feedback signal indicating that the force exerted on the at least one jaw element as measured by the sensor exceeds a predetermined threshold value. For example, when the force exceeds the predetermined threshold value, the tactile feedback device may provide a vibrating movement with a frequency high above the normal frequencies of pulsating tissue in a body. This may indicate to the user that the predetermined threshold value is exceeded.

In an embodiment, the elongate frame comprises a handle part and a shaft, wherein the trigger device is mounted on the handle part and the at least one jaw element is mounted on the shaft.

In an embodiment, the handle part comprises a housing, wherein the gripper device is arranged at a proximal side of the housing and wherein the tactile feedback device is arranged at the distal side of the housing. The proximal side of the housing is the side of the housing facing the proximal end of the surgical instrument, and the distal side of the housing is the side of the housing facing the distal end of the surgical instrument, e.g. the side of the housing facing towards the at least one jaw element.

In an embodiment, the handle part comprises a shaft locking mechanism to releasably lock the shaft to the handle part.

In an embodiment, the surgical instrument is a completely handheld instrument, wherein the surgical instrument comprises a battery to provide power to the surgical instrument.

In an embodiment, the surgical instrument comprises a battery holder to releasably hold the battery, wherein the battery holder is mounted on the elongate frame.

In an embodiment, the sensor is arranged in the trigger device.

In an embodiment, the trigger device comprises:
a trigger rotatably mounted in or on the elongate frame,
a translation element, for example a translation block, linearly guided in or on the elongate frame, and
a sensor support element, for example a sensor block, on which the sensor is mounted, wherein one side of the sensor support element is connected to the actuation rod and the other side of the sensor support element is connected to the translation element, wherein the trigger is connected to the translation element, wherein a rotation of the trigger causes a linear movement of the translation element which linear movement is transferred via the sensor support element to the actuator rod.

In this embodiment, the rotating movement of the trigger is converted in a linear movement of the translation element. The translation element is for example linearly guided by one or more linear guides, such as linear guiding pins mounted on the translation element that extend into linear guiding holes provided in a part of the elongate frame, such as a base element of the elongate frame. The linear movement of the translation element is transferred via a sensor support element to the actuation rod. Thus, the translation element, the sensor support element and the actuation rod move simultaneously in the same linear translation direction upon actuation of the trigger device by rotation of the trigger. This linear movement may provide a relatively low friction between the actuation rod and the sensor support element which may improve the measurement accuracy of the sensor mounted on the sensor support element. Thus, the linear movement of the translation element and the sensor support element may increase the sensitivity of the measurements of the sensor of the surgical instrument.

In an embodiment, the sensor support element is connected at one side to an actuation rod connection device configured to releasably connect the actuation rod and at the opposite side to the translation element. The actuation rod may also directly be connected to the sensor block.

In an embodiment, the tactile feedback device is connected to a switch, wherein the switch is arranged to switch the tactile feedback device on or off.

In an embodiment, the surgical instrument comprises a surgical tool, for example a cutting device, a cauterizing device, or an ablation device, The invention further provides the use of the surgical instrument according to any of the claims 1-18 to detect heartbeat related pulsation of tissue manipulated by the at least one jaw element of the surgical instrument.

It has been found that the surgical instrument of the invention is very suitable to determine heart beat related pulsation of tissue. This information is for example useful for the user, e.g. a surgeon, that carries out a surgical procedure, in which different tubular structures may have to be identified, in particular arteries have to be identified with respect to other tubular structures such as veins, urinary passages, biliary ducts, bronchial tubes, etc. The surgical instrument may also be applied in a minimally invasive surgical procedure in which tissue is manipulated by the surgical instrument, to facilitate cutting, cauterizing, ablation or other tissue removal or destruction with a corresponding surgical tool. When a pulsation of tissue manipulated, for example held, by the surgical instrument is measured by the surgical instrument and fed back to the tactile feedback device, this warns the surgeon that an artery is located close to the at least one jaw element of the surgical instrument. On the basis of this information, the surgeon can, when desired, change his course of action to avoid that, inadvertently, the artery is damaged by the surgical tool, or to prepare the artery for dissection, for example by cutting, by the surgical tool. The surgical tool, e.g. a cutting device, cauterizing device, ablation device or such, may be part of the surgical instrument itself, or may be provided as a separate device.

Surgical procedures in which the surgical instrument of the invention may advantageously be used for instance include laparoscopic hysterectomy, surgical procedures close to the ovaries and Fallopian tubes, such cystectomy of the ovaries, myomectomy, gastrointestinal surgery, cholecystectomy, (partial) nephrectomy, retroperitoneal lymph node dissection, pelvic lymph node dissection, prostatectomy, cardiothoracic surgery, vascular surgery, lobectomy and many other surgical procedures in which feedback with respect to heart beat related pulsation of tissue is desirable.

The invention further provides a method to detect pulsation of tissue, such as heartbeat related pulsation of tissue, comprising the steps of:
providing a surgical instrument according to any of the claims 1-18;
placing the at least one jaw element in contact with tissue; and
receiving tactile feedback using the tactile feedback device, wherein the tactile feedback provides feedback with respect to pulsation of the tissue.

In an embodiment, the method is used in a surgical procedure, as described above, for example a minimally invasive surgical procedure.

Further features and characteristics as described with respect to the surgical instrument of the invention may also be applied in the use and method of the invention.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF AN EMBODIMENT

Figure 1:
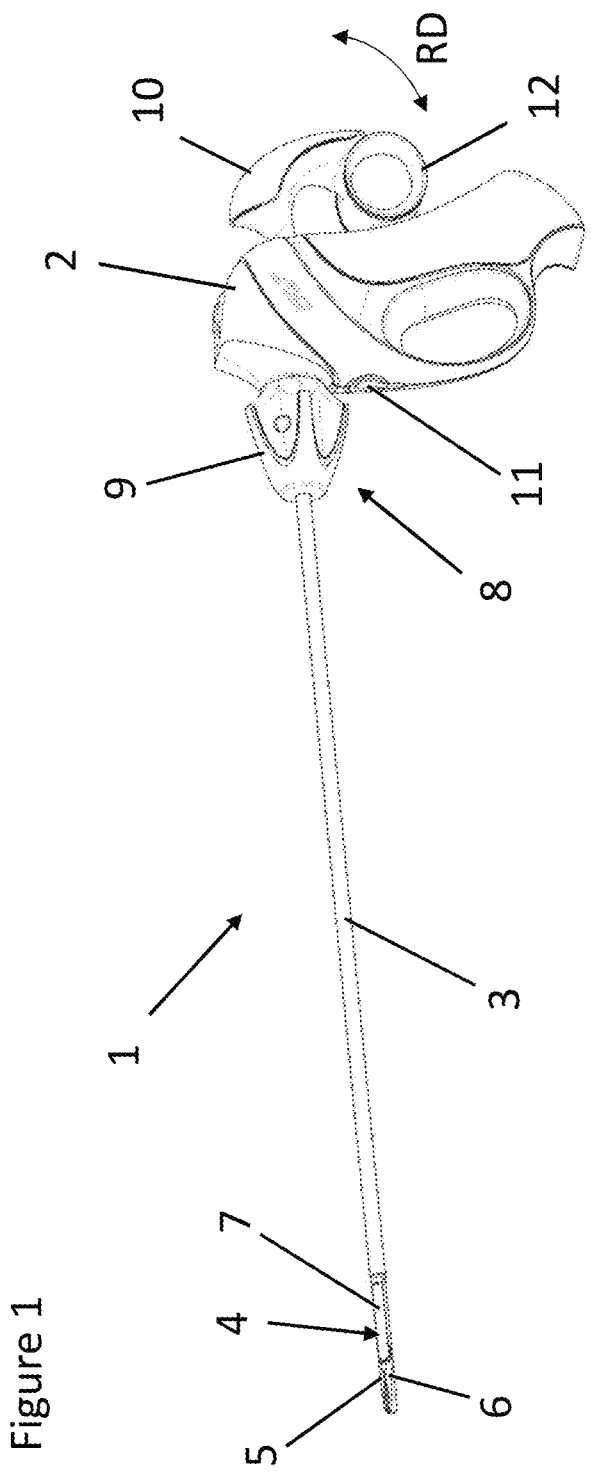
FIG. 1 shows a perspective view of a surgical instrument according to an aspect of the invention.

FIG. 1 shows a perspective of a surgical instrument for minimally invasive surgery, generally denoted by reference numeral 1.

The surgical instrument 1 comprises an elongate frame, formed by a handle part 2 and a shaft 3. The handle part 2 comprises an inner frame and a housing mounted on the inner frame. At the distal end of the shaft 3, a forceps construction 4 is provided. The forceps construction 4 comprises a first jaw element 5 and a second jaw element 6 that are rotatably mounted on a forceps frame 7 of the forceps construction 4.

The shaft 3 is releasably mounted on the handle part 2 with a shaft locking mechanism 8. Further, the shaft 3 is rotatable about its longitudinal axis with respect to the handle part 2. This allows different rotational positions of the jaw elements 5, 6, with respect to the handle part 2 of the surgical instrument 1. A rotation knob 9 is provided to manually set a rotation position of the shaft 3 with respect to the handle part 2.

The rotation of the shaft 3 about its longitudinal axis may for example be in the range of 300 degrees to 360 degrees, for example in the range of 160 degrees to 170 degrees in both rotation directions from a middle rotation position of the shaft 3. One or more stop elements may be provided to limit the range of rotation of the shaft 3. In an alternative embodiment, the shaft 3 may freely rotate in any direction about its longitudinal axis, i.e. without any limitation of the angle over which the shaft 3 may be rotated about its longitudinal axis.

A trigger 10 of a trigger device is provided at the proximal side of the handle part 2 to operate the jaw elements 5, 6 of the forceps construction 4. The trigger 10 is rotatably mounted in the handle part 2 of the surgical instrument 1.

A tactile feedback device 11 is provided at the distal side of the handle part 2. The tactile feedback device 11 is provided to provide feedback to the user with respect to the force that is exerted on the first jaw element 5 and/or the second jaw element 6.

The shaft 3 is hollow. Through the hollow shaft 3 an actuation rod extends from the trigger device to the actuation assembly of the forceps construction 1 to operate the forceps construction by manipulation of the trigger 10 in the rotation direction RD.

The surgical instrument 1 is a handheld device that can be held and operated by a single hand of a user.

The trigger 10 comprises a gripping ring 12 through which a thumb of the user may be placed. By movement of the gripping ring 12 away from the handle part 2, the trigger 10 may rotate with respect to the handle part 2 in the rotation direction RD. This rotation of the trigger 10 is transformed in an axial movement of the actuation rod in the hollow shaft 3. The axial movement of the actuation rod may cause the first jaw element 5 and the second jaw element 6 to rotate to an open position in which tissue can be arranged between the first jaw element 5 and the second jaw element 6.

By movement of the gripping ring 12 towards the handle part 2, the first jaw element 5 and the second jaw element 6 may from an open position in towards the closed position of the first jaw element 5 and the second jaw element 6 shown in FIG. 1.

The handle part 2 comprises a second gripping opening 35 through which at least one finger, typically all fingers of the same hand except the index finger, and optionally the middle finger are placed. The tactile feedback device 11 is arranged to receive the index finger or middle finger, for example a fingertip of the index finger or middle finger. Thus, the trigger 10 and the tactile feedback device 11 are arranged at opposite sides of the handle part 2, whereby the trigger 10 and the tactile feedback device 11 are associated with different fingers of the hand that operates and supports the surgical instrument 1.

The selected location of the tactile feedback device 11 is a central position of the handle part 2, i.e. on a longitudinal midplane of the handle part 2 such that the tactile feedback device 11 is equally well positioned for left handed and right handed users holding the surgical instrument 1. In other embodiments of the invention, the tactile feedback device 11 may be arranged at another location on the handle part 2, as long as the tactile feedback device 11 is not arranged on the trigger 10 of the trigger device.

Figure 2:
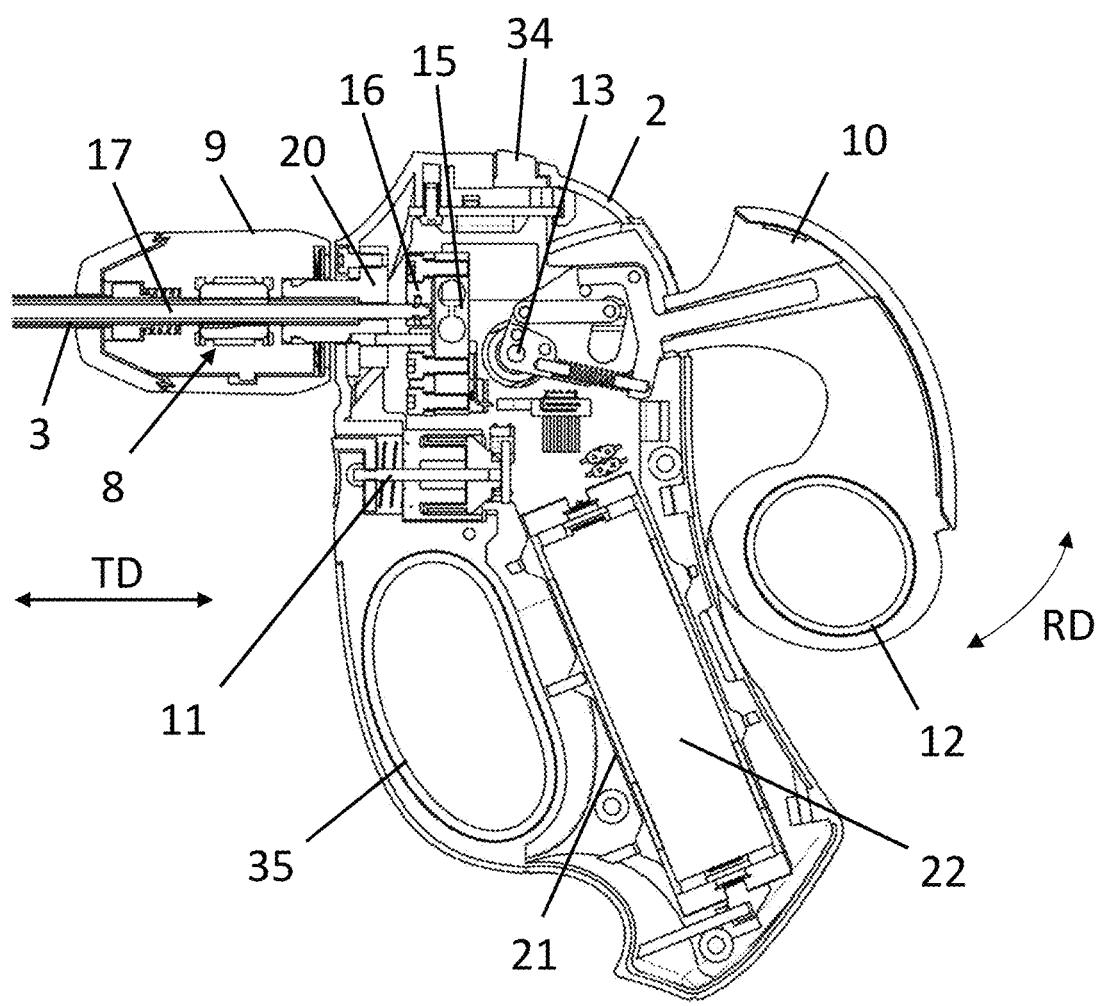
FIG. 2 shows a cross section of the handle part of the surgical instrument of FIG. 1.
Figure 3A:
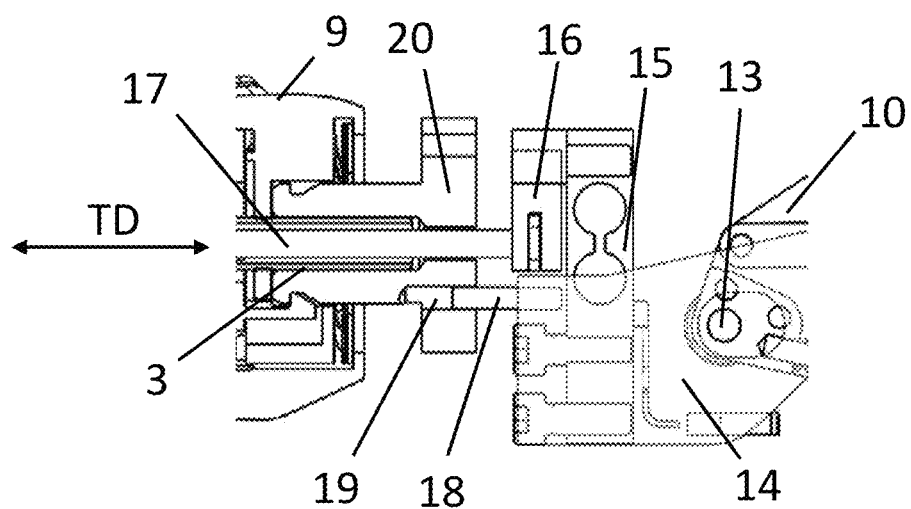
FIGS. 3a and 3b shows detail of the construction shown in FIG. 2.
Figure 3B:
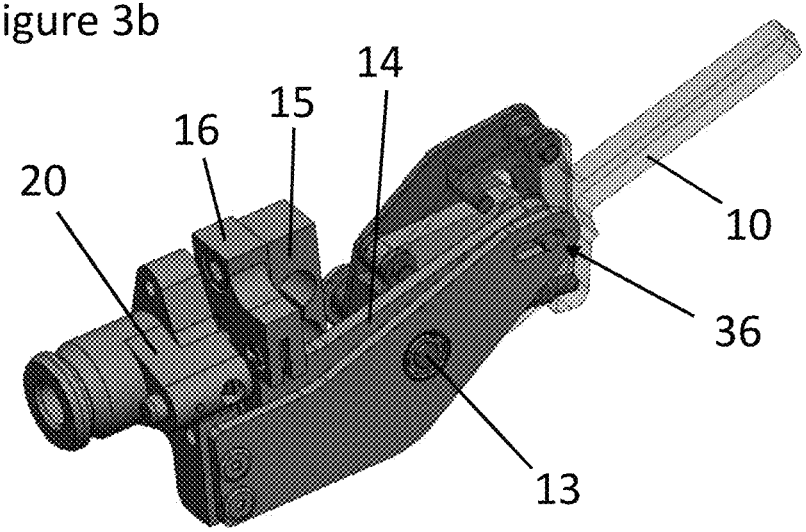

FIG. 2 shows a cross section of the handle part 2 showing the trigger device in more detail. The trigger device comprises the trigger 10 which is rotatably mounted about rotation axis 13. The trigger device further comprises a translation block 14 (see FIGS. 3a and 3b, not shown in FIG. 2), a sensor block 15 comprising one or more strain sensors and an actuation rod connection device 16. FIGS. 3a and 3b show these components of the trigger device in more detail.

Upon rotation of the trigger 10 about rotation axis 13, the translation block 14 will be moved in translation in a translation direction TD parallel to the longitudinal direction of the shaft 3 and the actuation rod 17 arranged in the hollow shaft 3. The sensor block 15 and the actuation rod connection device 16 are connected to the translation block 14 such that translation of the translation block 14 will also result of translation of the sensor block 15 and the actuation rod connection device 16 in the translation direction TD. The translation block 14 comprises a guiding pin 18 that extends in the translation direction TD. The end of the guiding pin 18 extends in a guiding channel 19 provided in a base element 20, which base element 20 is mounted on the handle part 2 of the surgical instrument 1. The guiding pin 18 guides the translation of the translation block 14, the sensor block 15 and the actuation rod connection device 16 in the translation direction TD. It is remarked that further linear guides 36 may be provided to guide this translation. In particular the translation block 14 may be guided by one or more guides in the translation direction TD.

Advantageously, no linear guides 36 are provided between the sensor block 14 and the base element 20 and/or between the actuation rod connection device 16 and the base element 20, since these linear guides may introduce friction between the sensor block 14 and the actuation rod 17. This friction may have a negative effect on the measurement accuracy of the sensors of the sensor block.

In or on the sensor block, the one or more strain sensors are provided. The one or more strain sensors are configured to measure a sensor signal representative for a force exerted on the first jaw element 5 and the second jaw element 6. The sensor block 15 is provided between the translation block 14 and the actuation rod connection device 1, whereby an lower end of the sensor block 15 is mounted to the translation block 14 and an upper end of the sensor block 15 is mounted to the actuation rod connection device 16.

Exertion of a force on the actuation rod 17, for example by tissue being pushed against the first jaw element or the second jaw element 6 transferred through the combination of the actuation rod connection device 16, sensor block 15 and translation block 14 will due to the connections of the sensor block 15 at the upper end and the lower end of the sensor block 15, respectively, will result in a deformation in the sensor block 14. This deformation may be measured by the strain sensors in the sensor block 15 such that the sensor signal provided by the strain sensors is representative for the force exerted on the first jaw element 5 and/or the second jaw element 6.

The sensor signal is guided to a controller in which the sensor signal is processed. On the basis of the sensor signal, the controller may provide a control signal that is fed to the tactile feedback device 11 to provide tactile feedback to the user.

The actuation rod connection device 16 is configured to releasably couple the actuation rod 17.

The surgical instrument 1 comprises a battery holder 21 holding a battery 22. The battery 22 is removable from the battery holder 21. All energy consumed by the surgical instrument 1 is provided by this battery 22. A tiltable or removable lid is provided in the housing of the handle part 2 that after opening/removal allows the battery 22 to be removed from the battery holder 21.

Figure 4:
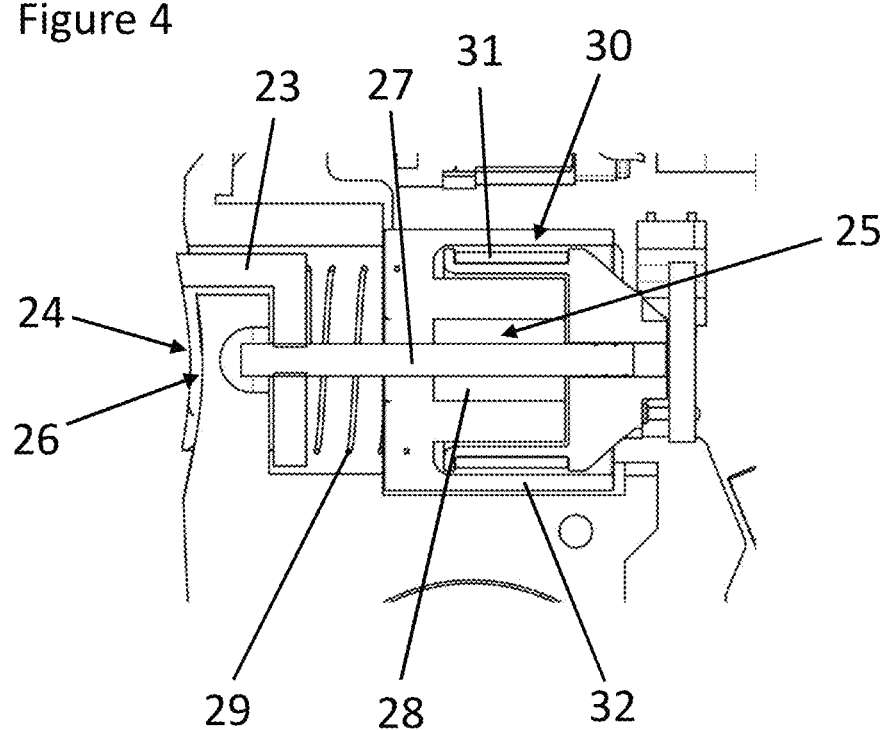
FIG. 4 shows a cross section of an embodiment of a tactile feedback device.
Figure 5:
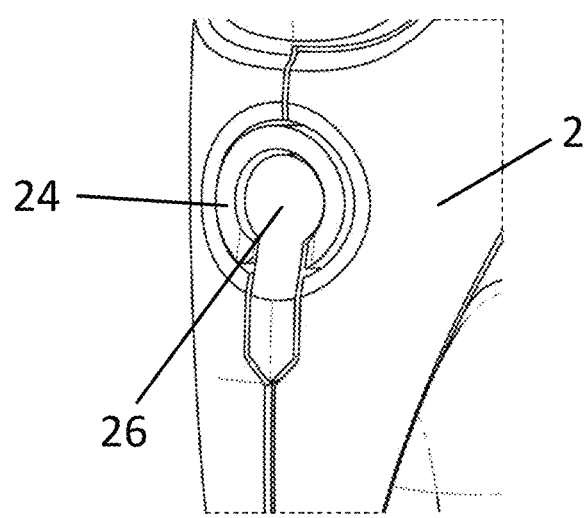
FIG. 5 shows a perspective view on the outside of the tactile feedback device of FIG. 4.

The tactile feedback device 11 is shown in more detail in FIGS. 4 and 5. FIG. 4 shows a longitudinal cross section of the tactile feedback device 11. FIG. 5 shows a perspective view on the outer side of the tactile feedback device 11 and a wall of the housing of the handle part 2 where the tactile feedback device 11 is provided.

The tactile feedback device 11 comprises a tactile element 23 to provide tactile feedback to the user. The tactile element 23 comprises a tactile end surface 24 on which a surface of a finger of a user, in particular a fingertip of an index finger or middle finger may be placed. The tactile end surface 24 has a horseshoe shape. The outer diameter of the horse shoe shape may for example be 4 mm to 18 mm, preferably 6 mm to 10 mm. The width of the tactile end surface 24 may for example be in the range of 0.5 mm to 3 mm, preferably 0.75 mm to 1.5 mm.

The tactile element 23 is supported by a tactile element guide 25. The guide end surface 26 may be formed by a wall of the housing of the handle part 2. A central part of the guide end surface 26 is surrounded at three sides by the tactile end surface 23 having the horseshoe shape.

The tactile element guide 25 provides a linear guiding for the tactile element 23. A rod element 27 of the tactile element 23 is arranged in a linear bearing 28 of the tactile element guide 25 to provide this linear guiding. The tactile element 23 is movable between an outer position, in which the tactile element 23 protrudes from the guide end surface 26, i.e. from the housing of the handle part 2, and an inner position in which the tactile element 23 is retracted in the housing of the handle part 2.

In FIGS. 4 and 5 the tactile element 23 is shown in the outer position. A spring 29 is provided to bias the tactile element 23 to the outer position of the tactile element 23. It can be seen that in this outer position of the tactile element 23, the tactile end surface 24 is spaced from the guide end surface 26. The distance between the tactile end surface 24 and the guide end surface 26 is for example 0.5 mm to 2 mm, preferably 0.75 mm to 1.5 mm, for example about 1 mm.

A feedback actuator 30 is provided to move the tactile element 23 within in the range of movement with respect to the tactile element guide 25. By actuation of the tactile element 23 using the feedback actuator 30 in the range of movement, the tactile end surface 24 may be pushed against the body part of the user arranged on the tactile end surface 24. The user will feel this pushing of the tactile element 23 on his fingertip.

When the user uses the tactile feedback device 11, he will put his fingertip on the tactile end surface 24 of the tactile element 23 and push it against the spring force of the spring 29 towards the inner position. Due to this inward movement, the tactile end surface 24 may become substantially flush with the guide end surface 26. Substantially flush means that the fingertip of the user, when properly arranged on the tactile feedback device 11, will have contact with both the tactile end surface 24 and the guide end surface 26. In the shown embodiment, a central area of the fingertip will be in contact with the central part of the guide end surface 26, while the area of the fingertip surrounding the central area will be in contact with the tactile end surface 24.

When touching simultaneously both the guide end surface 26 of the tactile element guide 25 and the tactile end surface 24 of the tactile element 23, movement of the tactile element 23 with respect to the tactile element guide 25 can be better perceived by the user.

It is remarked that the tactile end surface 24 and the guide end surface 26, when positioned to form a flush surface area, together may form a concave surface suitable to mate with an average sized convex surface of a fingertip of the index finger or middle finger of a user.

The feedback actuator 30 is a linear voice coil motor. The voice coil motor comprises a coil 31 and a permanent magnet 32. The linear voice coil motor is a suitable actuator 30 to move the tactile element 23 with respect to the tactile element guide 25 in order to provide suitable feedback to the user, for example feedback on heartbeat related pulsation of tissue touched by the first jaw element 5 and the second jaw element 6.

In alternative embodiments, other types of actuators, preferably linear actuators may be used to move the tactile element on the basis of the sensor signal. Examples of linear motor that may be applied in a tactile feedback device are a linear DC motor, a solenoid, a piezo motor, a shape memory alloy actuator. Other types of suitable motors may for example be a DC rotation motor, a voice coil rotation motor, a linear pneumatic or linear hydraulic motor.

The tactile feedback device, when activated uses energy, for example the voice coil motor needs energy to move the tactile element 23. This energy is provided by the battery 22. To prevent that energy is used when the tactile feedback device is not actively used, the tactile feedback device 11, in particular the voice coil motor 30 is only activated when the tactile element 23 is moved by the finger of the user against the spring force of the spring 29 out of the outer position towards the inner position. The spring 29 is provided to ensure that the tactile element 23 will be in the outer position when no force is exerted on the tactile element 23. The spring force may therefore be relatively low.

An activation sensor is provided to determine whether the tactile element 23 is in the outer position. The activation sensor may for example be an optical sensor that determines whether a sensor part provided on the tactile element 23 or the moving part of the actuator 30 is arranged between a light source and a light detector. The sensor part is aligned such that as soon the tactile element 23 is moved out of the outer position, the sensor part is no longer arranged between a light source and a light detector, such the light detector will receive the light emitted by the light source. Thus as soon as the tactile element 23 is moved out of the outer position, this will be measured by the activation sensor, and the feedback actuator 30 may be activated. An alternative activation sensor that can determine the position of the tactile element 23, or at least can determine whether the tactile element 23 is in the outer position may also be used.

It is remarked that to save energy, the strain sensors may also only be energized when the activation sensor has determined that the tactile element 23 is moved out of the outer position.

Furthermore, an on/off switch 34 is arranged at the top side of the handle part 2. This on/off switch allows to switch the device completely off, when not used to save energy of the battery 22.

The tactile feedback device 11 of the invention may be used to provide tactile feedback of heartbeat related pulsation of tissue manipulated by the first jaw element 5 and/or the second jaw element 6. This heartbeat related pulsation is very useful information for a surgeon. To ensure that the heartbeat related pulsation is felt by the user, the different components of the feedback loop, such as the sensor, a controller and the tactile feedback device, for example an actuator of the tactile feedback device are provided with sufficient bandwidth to provide feedback on the heart beat related pulsation of tissue.

Surgical procedures in which the surgical instrument of the invention may advantageously be used for instance include laparoscopic hysterectomy, surgical procedures close to the ovaries and Fallopian tubes, such cystectomy of the ovaries, myomectomy, gastrointestinal surgery, cholecystectomy, (partial) nephrectomy, retroperitoneal lymph node dissection, pelvic lymph node dissection, prostatectomy, cardiothoracic surgery, vascular surgery, lobectomy and many other surgical procedures in which feedback with respect to heart beat related pulsation of tissue is desirable.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below. It will further be appreciated that several mechanical layouts of the forceps are possible within the concept of the invention provided a slit or any other opening is arranged between the jaws of the forceps, said opening being arranged to guide the jaw reaction forces to separate parts of the frame of the surgical instrument.

The invention claimed is:

1. A surgical instrument, for example surgical instrument for minimally invasive surgery, comprising:
   an elongate frame,
   at least one jaw element mounted movably at a distal end of the elongate frame,
   a trigger device to operate the at least one jaw element and arranged at a proximal end of the elongate frame,
   an actuation rod provided between the trigger device and the at least one jaw element to transfer movement of the trigger device to the at least one jaw element,
   a sensor to provide a sensor signal representative for a force exerted on the at least one jaw element, and
   a tactile feedback device to provide tactile feedback to the user on the basis of the sensor signal, wherein the tactile feedback device is mounted on the elongate frame,
   wherein the tactile feedback device comprises:
   a rigid tactile element to provide tactile feedback to the user,
   a tactile element guide supporting the rigid tactile element, wherein the rigid tactile element is linearly movable with respect to the tactile element guide in a range of movement between an outer position and an inner position, and
   a linear feedback actuator arranged to move the rigid tactile element within in the range of movement with respect to the tactile element guide,
   wherein the rigid tactile element has a tactile end surface and wherein the tactile element guide comprises a guide end surface, wherein in one position of the rigid tactile element the guide end surface is flush with the tactile end surface and that at least in this position of the rigid tactile element a body part of the user placed on the rigid tactile element will be in contact with both the guide end surface and the tactile end surface.

2. The surgical instrument of claim 1, wherein the tactile end surface comprises one or more surface areas, wherein the one or more surface areas of the tactile end surface are provided at at least two opposite sides of at least one surface area of the guide end surface, wherein the one or more surface areas of the tactile end surface and the at least one surface area of the guide end surface are designed to be simultaneously touched by a single finger tip of a user, when the rigid tactile element is arranged in the one position in which the guide end surface is flush with the tactile end surface.

3. The surgical instrument of claim 2, wherein the tactile end surface comprises a horse shoe shape or partly annular shape.

4. The surgical instrument of claim 1, wherein the feedback actuator comprises a linear voice coil actuator.

5. The surgical instrument of claim 1, wherein the rigid tactile element is biased by a biasing element in the outer position.

6. The surgical instrument of claim 5, wherein the tactile feedback device comprises an activation sensor, wherein the activation sensor is arranged to determine whether the rigid tactile element is arranged in the outer position, and wherein the tactile feedback device is configured to be deactivated when the rigid tactile element is arranged in the outer position and wherein the tactile feedback device is configured to be activated when the rigid tactile element is not arranged in the outer position.

7. The surgical instrument of claim 1, wherein a bandwidth of the tactile feedback device is designed to provide tactile feedback of heartbeat related pulsation of tissue manipulated by the at least one jaw element.

8. The surgical instrument of claim 1, wherein the trigger device comprises a trigger having a gripping element designed to receive a thumb of the user, wherein the gripping element is arranged at a proximal side of the surgical instrument.

9. The surgical instrument of claim 1, wherein the elongate frame comprises a handle part and a shaft, wherein the trigger device and the actuator are mounted on the handle part and the at least one jaw element is mounted on the shaft.

10. The surgical instrument of claim 9, wherein the handle part comprises a housing, wherein the trigger device is arranged at a proximal side of the housing and wherein the tactile feedback device is arranged at the distal side of the housing.

11. The surgical instrument of claim 9, wherein the handle part comprises a shaft locking mechanism to releasably lock the shaft to the handle part.

12. The surgical instrument of claim 1, wherein the surgical instrument is a completely handheld instrument, wherein the surgical instrument comprises a battery to provide power to the surgical instrument.

13. The surgical instrument of claim 1, wherein the surgical instrument comprises a battery holder to releasably hold the battery, wherein the battery holder is mounted on the elongate frame.

14. The surgical instrument of claim 1, wherein the sensor is arranged in the trigger device.

15. The surgical instrument of claim 1, wherein the trigger device comprises:
   a trigger rotatably mounted in or on the elongate frame,
   a translation element linearly guided in or on the elongate frame, and a sensor support element on which the sensor is mounted, wherein one side of the sensor support element is connected to the actuation rod and the other side of the sensor support element is connected to the translation element, wherein the trigger is connected to the translation element, wherein a rotation of the trigger causes a linear movement of the translation element, which linear movement is transferred via the sensor support element to the actuator rod.

16. The surgical instrument of claim 1, wherein the tactile feedback device is connected to a switch, wherein the switch is arranged to switch the tactile feedback device on or off.

17. A method of detecting heartbeat, comprising:
utilizing the surgical instrument of claim 1 to detect heartbeat related pulsation of tissue manipulated by the at least one jaw element of the surgical instrument.

18. A method to detect pulsation of tissue, such as heartbeat related pulsation of tissue, comprising the steps of:
providing a surgical instrument according to claim 1;
placing the at least one jaw element in contact with tissue; and
receiving tactile feedback using the tactile feedback device, wherein the tactile feedback provides feedback with respect to pulsation of the tissue.

19. The method of claim 18, wherein the method is used in a minimally invasive surgical procedure.

20. A surgical instrument, for example surgical instrument for minimally invasive surgery, comprising:
an elongate frame,
at least one jaw element mounted movably at a distal end of the elongate frame,
a trigger device to operate the at least one jaw element and arranged at a proximal end of the elongate frame,
an actuation rod provided between the trigger device and the at least one jaw element to transfer movement of the trigger device to the at least one jaw element,
a sensor to provide a sensor signal representative for a force exerted on the at least one jaw element, and
a tactile feedback device to provide tactile feedback to the user on the basis of the sensor signal, wherein the tactile feedback device is mounted on the elongate frame,
wherein the tactile feedback device comprises:
a tactile element to provide tactile feedback to the user,
a tactile element guide supporting the tactile element, wherein the tactile element is linearly movable with respect to the tactile element guide in a range of movement between an outer position and an inner position, and
a linear feedback actuator arranged to move the tactile element within in the range of movement with respect to the tactile element guide,
wherein the tactile element has a tactile end surface and wherein the tactile element guide comprises a guide end surface, wherein in at least one position of the tactile element the guide end surface is substantially flush with the tactile end surface such that in this position of the tactile element a body part of the user placed on the tactile element will be in contact with both the guide end surface and the tactile end surface,
wherein the tactile end surface comprises one or more surface areas, wherein the one or more surface areas of the tactile end surface are provided at at least two opposite sides of at least one surface area of the guide end surface, wherein the one or more surface areas of the tactile end surface and the at least one surface area of the guide end surface are designed to be simultaneously touched by a single finger tip of a user, when the tactile element is arranged in the at least one position in which the guide end surface is substantially flush with the tactile end surface, wherein the at least one surface area of the guide end surface forms a central part to contact a central area of the fingertip and the one or more surface areas of the tactile end surface surround the central part to contact an area of the fingertip surrounding the central area.

21. The surgical instrument of claim 20, wherein the tactile end surface comprises a horse shoe shape or partly annular shape.

22. The surgical instrument of claim 20, wherein the feedback actuator comprises a linear voice coil actuator.

23. The surgical instrument of claim 20, wherein the tactile element is biased by a biasing element in the outer position.

24. The surgical instrument of claim 23, wherein the tactile feedback device comprises an activation sensor, wherein the activation sensor is arranged to determine whether the tactile element is arranged in the outer position, and wherein the tactile feedback device is configured to be deactivated when the tactile element is arranged in the outer position and wherein the tactile feedback device is configured to be activated when the tactile element is not arranged in the outer position.

25. A method of detecting heartbeat, comprising:
utilizing the surgical instrument of claim 20 to detect heartbeat related pulsation of tissue manipulated by the at least one jaw element of the surgical instrument.

26. A method to detect pulsation of tissue, such as heartbeat related pulsation of tissue, comprising the steps of:
providing a surgical instrument according to claim 20;
placing the at least one jaw element in contact with tissue; and
receiving tactile feedback using the tactile feedback device, wherein the tactile feedback provides feedback with respect to pulsation of the tissue.

27. The method of claim 26, wherein the method is used in a minimally invasive surgical procedure.

* * * * *